(12) United States Patent
Bearman et al.

(10) Patent No.: US 7,768,641 B2
(45) Date of Patent: *Aug. 3, 2010

(54) SPATIAL IMAGE MODULATION TO IMPROVE PERFORMANCE OF COMPUTED TOMOGRAPHY IMAGING SPECTROMETER

(75) Inventors: Gregory H. Bearman, Pasadena, CA (US); Daniel W. Wilson, Montrose, CA (US); William R. Johnson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 11/657,936

(22) Filed: Jan. 24, 2007

(65) Prior Publication Data

US 2007/0182962 A1 Aug. 9, 2007

Related U.S. Application Data

(60) Provisional application No. 60/762,004, filed on Jan. 24, 2006.

(51) Int. Cl.
*G01J 3/28* (2006.01)
(52) U.S. Cl. ..................... 356/328
(58) Field of Classification Search ............. 356/328
See application file for complete search history.

(56) References Cited

U.S. PATENT DOCUMENTS 5,159,199 A * 10/1992 LaBaw ............ 250/339.02
5,760,899 A * 6/1998 Eismann ............ 356/326
6,104,488 A * 8/2000 LeVan ............ 356/328
6,522,403 B2 * 2/2003 Wilson et al. ............ 356/328
7,092,088 B2 * 8/2006 Schau ............ 356/328
2002/0175286 A1 * 11/2002 Murguia ............ 250/339.07
2006/0050391 A1 * 3/2006 Backlund et al. ............ 359/573
2006/0158645 A1 * 7/2006 Maier et al. ............ 356/301
2006/0274308 A1 * 12/2006 Brady et al. ............ 356/326

OTHER PUBLICATIONS

Hartke et al., "Hyperspectral-dual spectral region imaging spectrometer," *Proceedings of SPIE*, vol. 5563, pp. 156-166, 2004.
Johnson et al., "All-reflective snapshot hyperspectral imager for ultraviolet and infrared application," *Optics Letters*, vol. 30, No. 12, Jun. 15, 2005.
Hartke et al., "Non-scanning dual infrared band hyperspectral imaging spectrometer design," *Proceedings of SPIE*, vol. 6295, 12 pages, 2006.
Johnson et al., "Spatial-spectral modulating snapshot hyperspectral imager," *Applied Optics*, vol. 45, No. 9, Mar. 20, 2006, pp. 1898-1908.

* cited by examiner

*Primary Examiner*—Kara E Geisel
(74) *Attorney, Agent, or Firm*—Christie, Parker & Hale, LLP

(57) ABSTRACT

Computed tomography imaging spectrometers ("CTIS"s) having patterns for imposing spatial structure are provided. The pattern may be imposed either directly on the object scene being imaged or at the field stop aperture. The use of the pattern improves the accuracy of the captured spatial and spectral information.

21 Claims, 16 Drawing Sheets

OBJECT SCENE
THREE SPOTS:
RED(R), BLUE(B),
WHITE(W) COMPOSED OF
blue(b), green(g),
yellow(y), red(r)

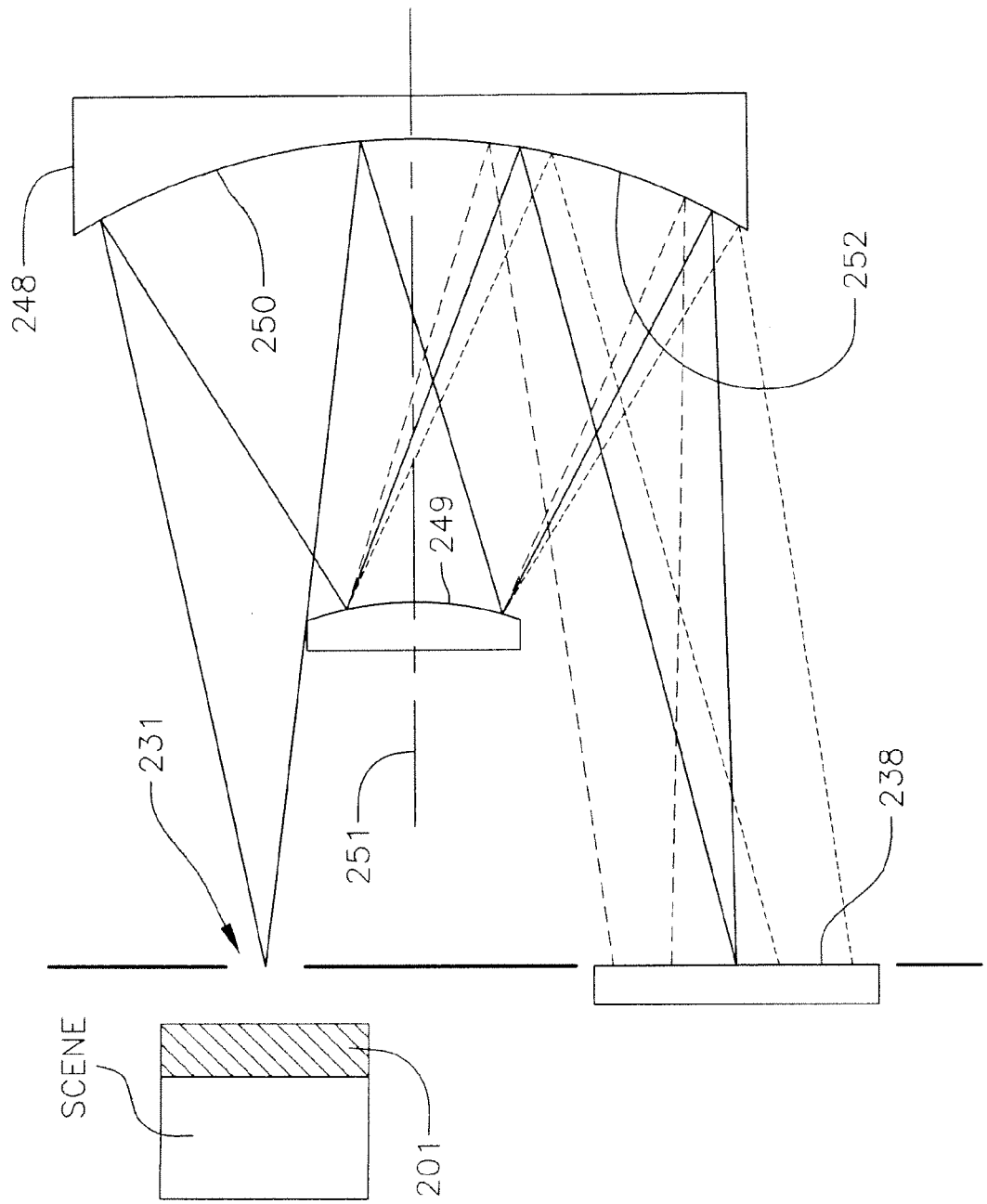

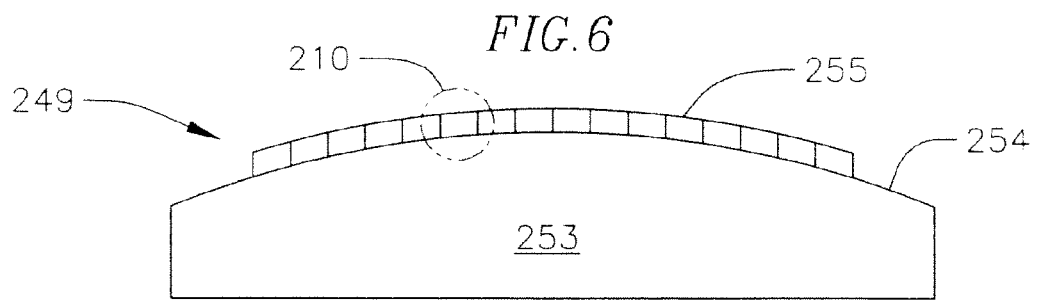
FIG.6
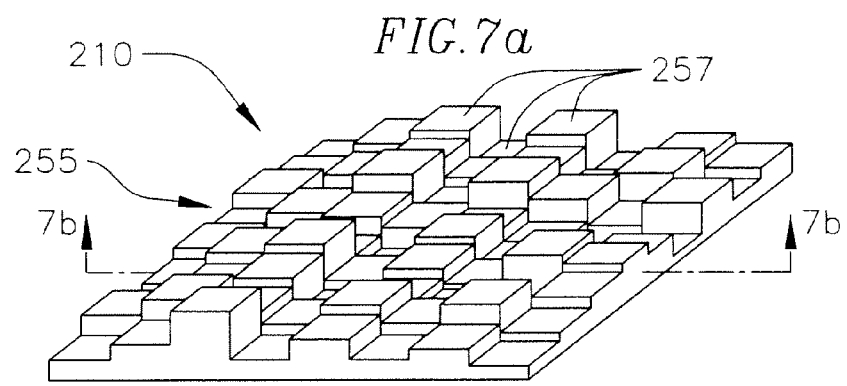
FIG.7a
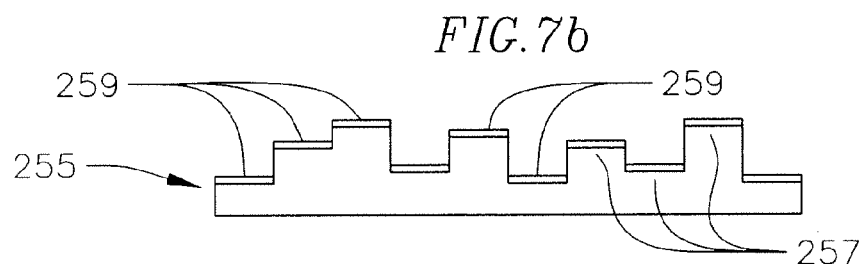
FIG.7b
FIG.7c
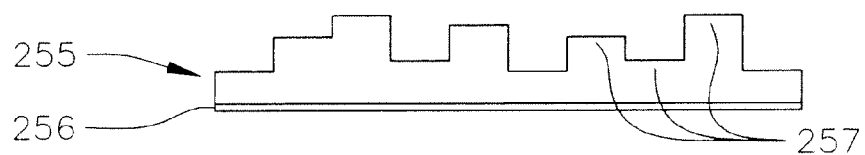
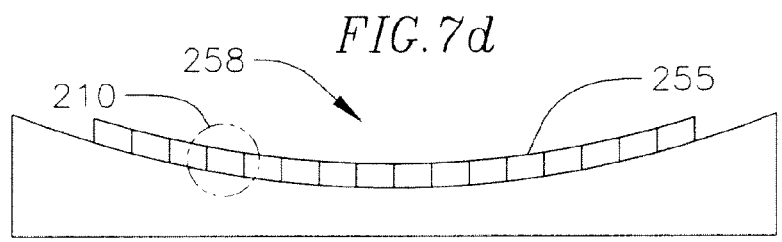
FIG.7d

SPATIAL IMAGE MODULATION TO IMPROVE PERFORMANCE OF COMPUTED TOMOGRAPHY IMAGING SPECTROMETER

CROSS REFERENCE TO RELATED APPLICATION

This application claims priority to and the benefit of U.S. Provisional Patent Application No. 60/762,004 titled "SPATIAL IMAGE MODULATION TO IMPROVE PERFORMANCE OF COMPUTED TOMOGRAPHY IMAGING SPECTROMETER," filed on Jan. 24, 2006 in the United States Patent and Trademark Office, the entire content of which is incorporated herein by reference.

STATEMENT REGARDING FEDERALLY SPONSORED RESEARCH OR DEVELOPMENT

The invention described herein was made in the performance of work under a NASA contract, and is subject to the provisions of Public Law 96-517 (35 U.S.C §202) in which the Contractor has elected to retain title.

FIELD OF THE INVENTION

The invention is directed to improved computed tomography imaging spectrometers for improving spatial-spectral image accuracy.

BACKGROUND OF THE INVENTION

The computed tomography imaging spectrometer ("CTIS") enables spectral imaging of transient events by capturing spatial and spectral information in a single snapshot. That is, the CTIS captures spatial and spectral information from a two-dimensional ("2D") scene in a single image frame.

In a typical CTIS, as shown in FIGS. 1-3, spots of visible light, namely a blue spot B, a red spot R, and a white spot W, in the field stop 41 are collimated in a lens 32, filtered through a wide-band filter means 33, and passed through a 2D grating disperser 34 which produces a 2D array of diffraction orders 35. A final focusing element, such as a lens 36, re-images the various diffraction orders of light 37 onto a FPA detector 38 (e.g. a charge coupled device ("CCD")) that records the intensity but not the color of the incident light. Each diffraction order transmitted from the grating disperser 34 produces a spectrally dispersed image 44 of the scene, except for the undiffracted "zeroth" order which produces an undispersed image in the dashed center area 45 of the FPA detector 44, as illustrated best in FIG. 3.

Current systems are generally either slit imaging spectrometers or bandpass-filter imaging spectrometers. However, slit imaging spectrometers must scan the scene spatially to build up a 2D image, and bandpass-filter imaging spectrometers must scan the scene spectrally. The CTIS captures the scene's spatial and spectral information by imaging the scene through a 2D grating disperser, as discussed above and illustrated in FIGS. 1-3. This produces multiple, spectrally dispersed images of the scene that are recorded by a focal plane array ("FPA") detector. From the captured intensity pattern, computed-tomography algorithms can be used to reconstruct the scene into a cube of spatial (x and y) and spectral (wavelength) information.

The non-scanning nature of the CTIS enables transient-event imaging spectrometry and thus opens up new applications that were previously impossible due to scene movement/evolution during scanning. These include for example: 1) spectral imaging of living biological systems that move/change rapidly during an experiment (e.g. cells, retina, colon, etc.); 2) industrial processes such as semiconductor etching; 3) defense surveillance of regions in which neither the location nor the time of an explosion, missile launch, or chem-bio weapon deployment is known. In addition, the CTIS can be used for static scene spectral imaging when the spatial and spectral resolution requirements are not too demanding.

Current imaging spectrometers use monochrome cameras for capturing the spectrally dispersed images that are used to reconstruct the spatial-spectral information in the scene being imaged. Monochrome camera CTIS systems have scene-dependent spectral resolution and tomographic reconstruction artifacts. This is largely because the reconstruction algorithm does not have enough information to effectively sort out the overlapping information in the spectrally dispersed diffraction images. Scenes that do not have significant spatial or spectral diversity pose a unique challenge. In these scenes, the dispersed images are very smooth, without structural features. This lack of structure causes the reconstruction algorithm to stagnate with a poor solution to the spatial-spectral data cube because a poor solution has nearly the same error as the correct solution. In other words, the reconstruction merit function for these types of scenes has a very broad minimum, so poor solutions are not effectively rejected. As a result, the spectra reconstruction is suitable at the edges of the field, but poor away from the edges.

SUMMARY OF THE INVENTION

In one embodiment of the present invention, a transmissive CTIS generally includes a focal plane array ("FPA") detector, a primary imaging lens, a 2D grating disperser, a collimating lens and a pattern placed within the system optics. In another embodiment of the present invention, a reflective CTIS includes a 2D object scene aperture, an unitary primary mirror assembly having a first concave mirror and a second concave mirror, a 2D reflective convex diffraction grating having an axis, a FPA detector and a pattern imposed within the system optics.

The pattern placed within the system optics imposes spatial structure in the image. This extra spatial structure dramatically improves the spectral reconstruction any where in the field. The pattern may be placed either directly over the object being imaged, or at the aperture field stop.

In an alternative embodiment, in either the transmissive or reflective CTIS systems, the FPA detector may be a color FPA detector. The color FPA detector can take a number of forms. For example, in one embodiment, the color FPA detector may comprise a digital color camera including a digital image sensor, such as a Foveon X3® digital image sensor or a Bayer color filter mosaic. The Foveon X3® digital image sensor includes three layers of pixels (i.e. one red layer, one blue layer and one green layer) on top of each other embedded in a silicon sensor. The Bayer color filter mosaic includes a single layer of a repeating array of red, green and blue filter material deposited on top of each spatial location, and the Bayer color filter mosaic uses twice as many green filters as red or blue filters. In another embodiment, the color FPA detector may include three charge coupled devices ("CCDs"), one for each color: red, green and blue.

BRIEF DESCRIPTION OF THE DRAWINGS

These and other features and advantages of the present invention will be better understood by reference to the following detailed description when considered in conjunction with the accompanying drawings in which:

FIG. 5a is a schematic of the principal optical components of a reflective CTIS according to one embodiment of the present invention;

FIG. 6 is an enlarged view of the grating cells of the 2D reflective convex diffraction grating of FIGS. 5a and 5b;

FIG. 7a is a greatly enlarged and detailed three-dimensional view of area 210 of FIG. 6;

FIG. 7b is a detailed 2D view through plane 7b-7b of FIG. 7a;

FIG. 7c is a detailed 2D view of another cell, similar to that of FIG. 7b, but with the mirror surface on the back side of the cell;

FIG. 7d is an enlarged view of grating cells, similar to that of FIG. 6, but on a 2D reflective concave diffraction grating;

DETAILED DESCRIPTION OF THE INVENTION

The computed tomography imaging spectrometer ("CTIS") operates by multiplexing the spectral and spatial data of an image onto a focal plane, which captures all the information in a single snapshot. It is this feature that allows video rate spectral imaging. Spectra are obtained by means of tomographic reconstruction, leading to the naming of the instrument as a computed-tomography imaging spectrometer.

The CTIS uses a field stop aperture in the optical train to define the field of view. According to one embodiment of the present invention, the recovered spectra are improved by imposing spatial structure in the image. This spatial structure may be imposed either directly on the scene being imaged or at the field stop aperture. The spatial structure can be used in both transmissive and reflective CTIS systems.

Transmissive CTIS

Figure 1:
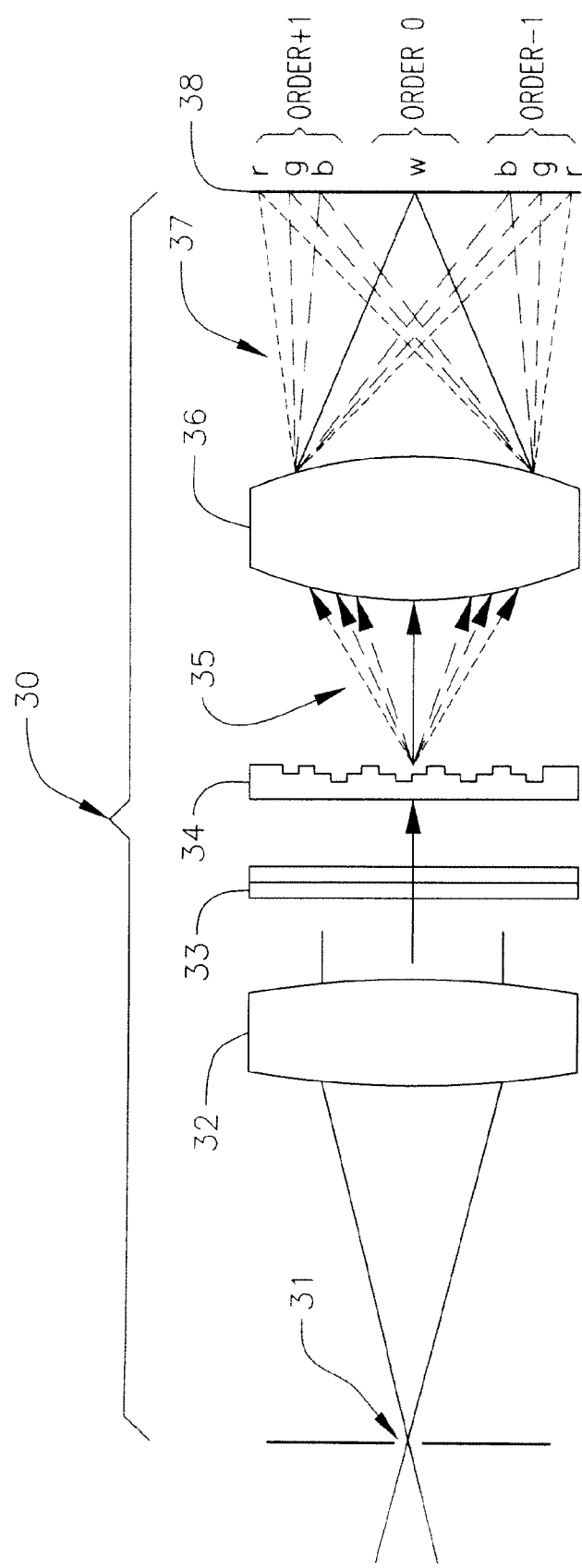
FIG. 1 is an optical layout of a prior art CTIS system.
Figure 3:
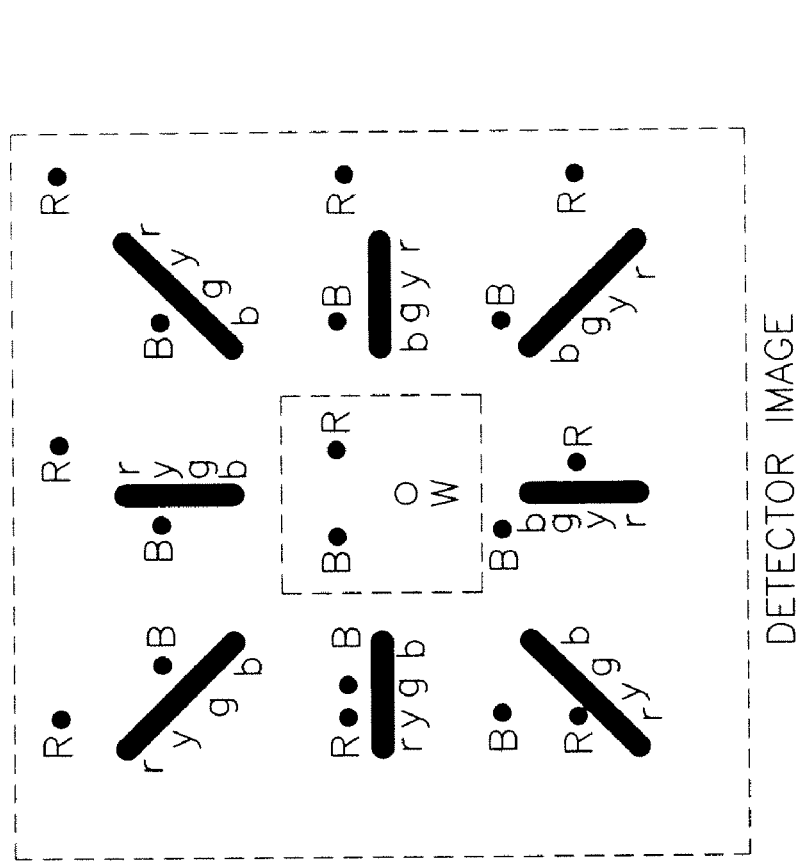
FIG. 3 is a schematic depicting how the scene of FIG. 2 is dispersed by the CTIS system of FIG. 1 having a 3×3 grating disperser, and further demonstrating that each dispersed image provides unique information about the scene.
Figure 2:
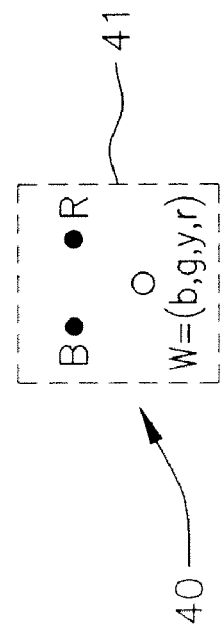
FIG. 2 is a field stop scene composed of blue, red and white dots.
Figure 4A:
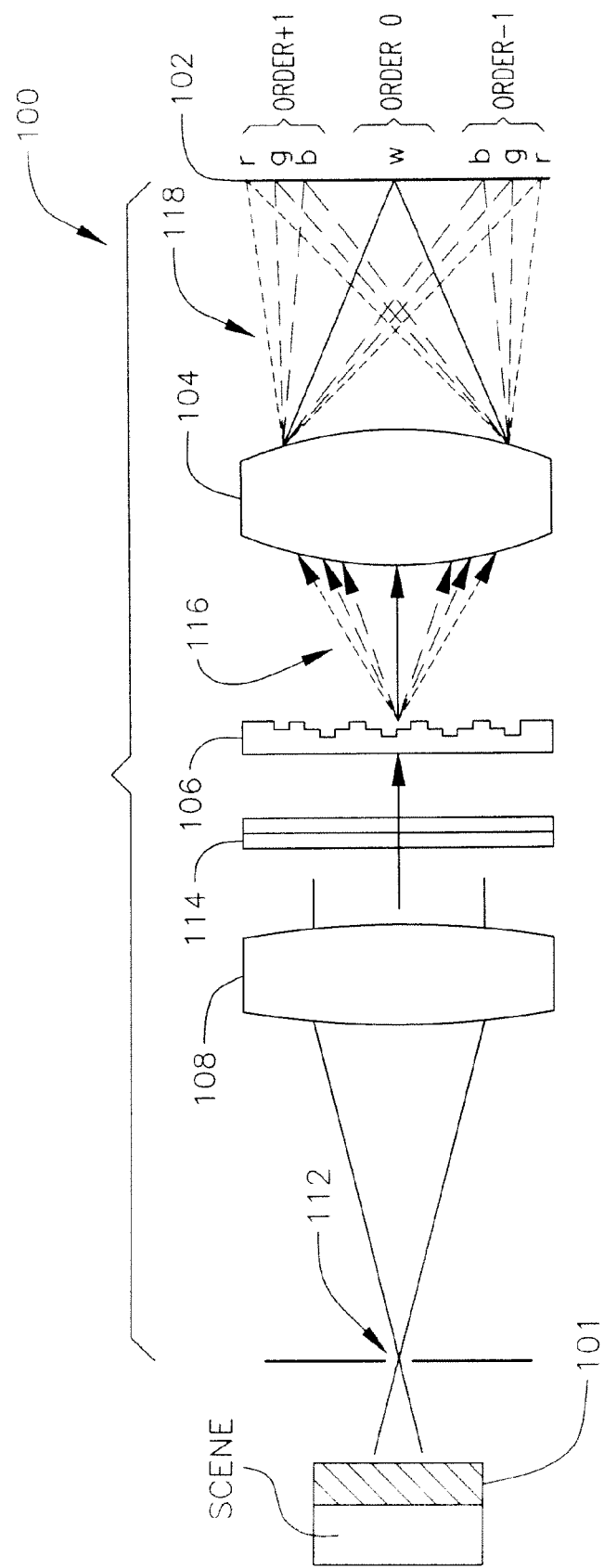
FIG. 4a is an optical layout of a transmissive CTIS system according to one embodiment of the present invention.
Figure 4B:
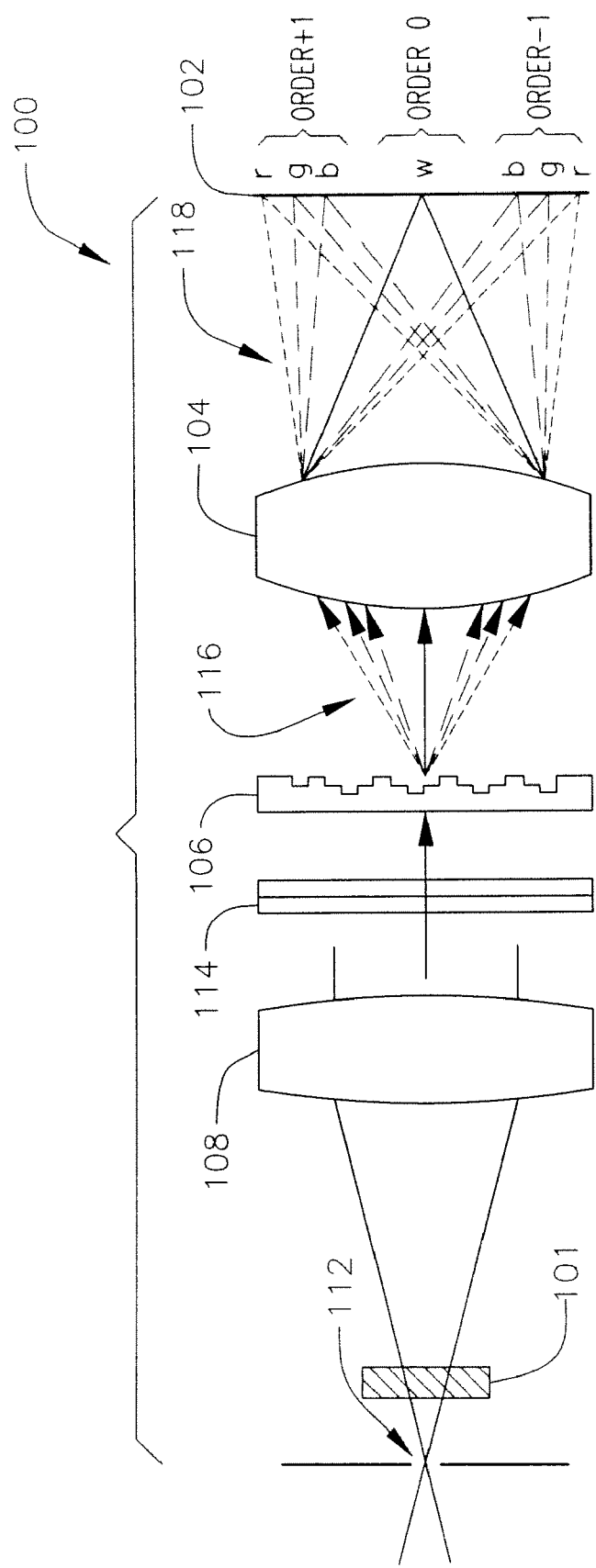
FIG. 4b is an optical layout of a transmissive CTIS system according to another embodiment of the present invention.

In one embodiment of the present invention, as illustrated in FIGS. 4a and 4b, a transmissive CTIS 100 generally includes a focal plane array ("FPA") detector 102, a primary imaging lens 104, a 2D grating disperser 106, a collimating lens 108 and a pattern 101 for imposing spatial structure.

In operation, a primary optical system (such as a telescope, microscope, endoscope, etc.) forms a real image of the scene on a rectangular aperture 112 serving as a field stop (shown in FIG. 5). Light in the field stop 112 is collimated in the collimating lens 108, filtered through a wide-band filter means 114 and passed through the 2D grating disperser, which produces a 2D array of diffraction orders 116. The imaging lens 104 then re-images the diffraction orders of light 118 onto the FPA detector 102 which records the intensity of the incident light. Each diffraction order 118 transmitted from the 2D grating disperser 106 produces a spectrally dispersed image 120 of the scene, except for the undiffracted "zeroth" order which produces an undispersed image in the center of the FPA detector 102.

To impose spatial structure in the image, the pattern 101 may be placed either directly on the scene being imaged, as shown in FIG. 4a, or at the field stop aperture 112, as shown in FIG. 4b. The pattern 101 may include any suitable pattern, nonlimiting examples of which include checkerboard patterns and grid patterns. The pattern 101 may also take any suitable form for inclusion in the CTIS. In one embodiment, for example, the pattern 101 comprises an opaque mask which can be placed at the field stop aperture or projected directly on the object to be imaged.

In an alternative embodiment, the FPA detector 102 is a color FPA detector. The color FPA detector can take a number of forms and is described in co-pending U.S. patent application titled "COLOR CAMERA COMPUTED TOMOGRAPHY IMAGING SPECTROMETER FOR IMPROVED SPATIAL-SPECTRAL IMAGE ACCURACY," filed Dec. 12, 2006, the entire content of which is incorporated herein by reference. For example, in one embodiment, the color FPA detector 238 may comprise a digital color camera including a digital image sensor, such as a Foveon X3® digital image sensor or a Bayer color filter mosaic. The Foveon X3® digital image sensor includes three layers of pixels (i.e. one red layer, one blue layer and one green layer) on top of each other embedded in a silicon sensor. The Bayer color filter mosaic includes a single layer of a repeating array of red, green and blue filter material deposited on top of each spatial location, and the Bayer color filter mosaic uses twice as many green filters as red or blue filters. In another embodiment, the color FPA detector 238 may include three charge coupled devices ("CCDs"), one for each color: red, green and blue.

In still another embodiment, the color FPA detector may comprise any suitable device, such as a monochrome camera or a color camera, over which is positioned a transmission filter that performs a user-defined transmissive function. For example, a color filter adapted to transmit a single color (e.g. red, green or blue) can be positioned over the FPA detector.

Reflective CTIS

Transmissive CTIS systems are not ideal for operation in the ultraviolet and infrared portions of the spectrum because there are few materials that transmit well. For this reason, the reflective CTIS has been developed. The reflective CTIS employs an Offner design and is generally described in U.S. Pat. No. 6,522,403 to Wilson, et al., issued Feb. 18, 2003, the entire content of which is incorporated herein by reference.

Figure 5B:
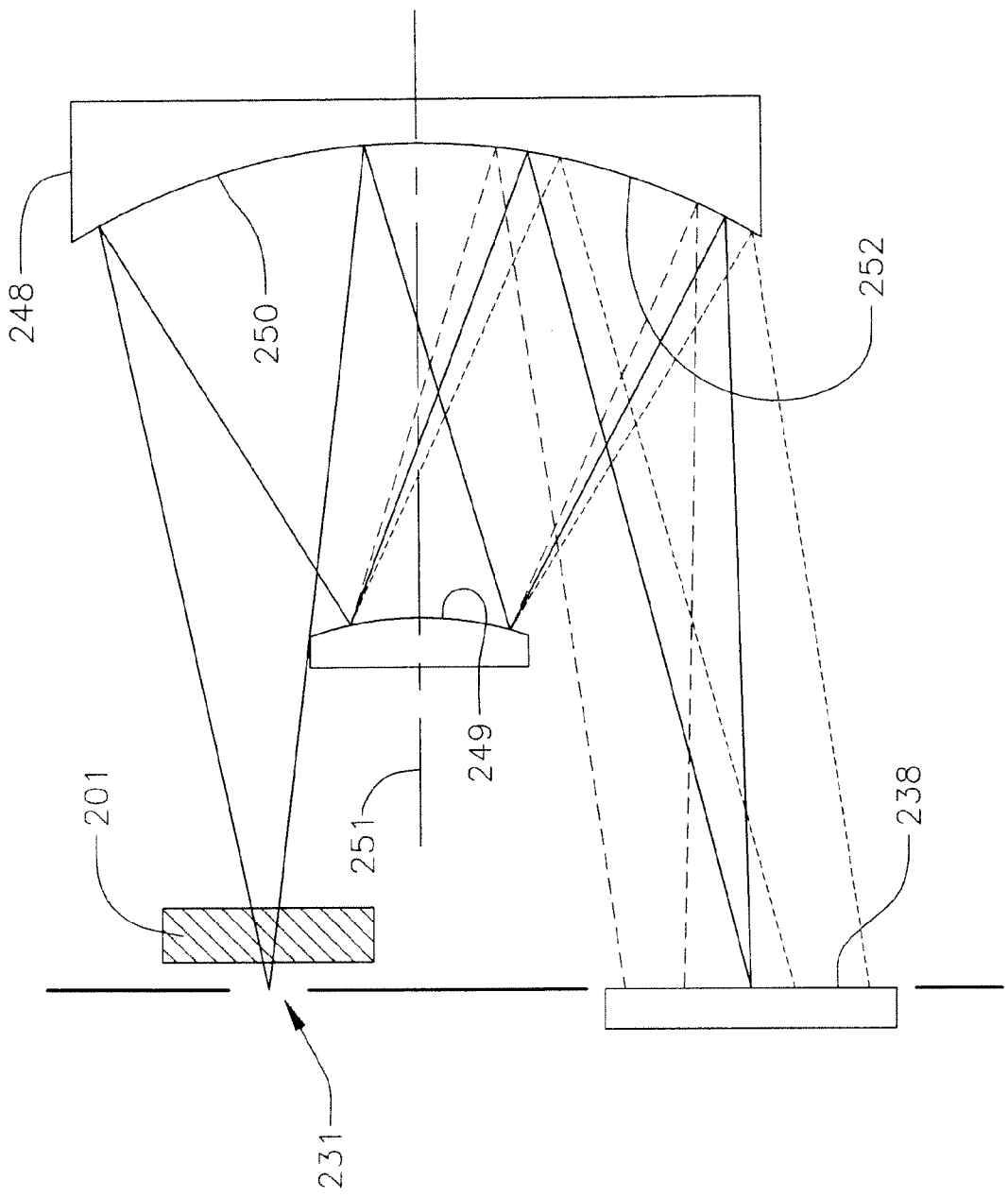
FIG. 5b is a schematic of the principal optical components of a reflective CTIS according to another embodiment of the present invention.

As shown in FIGS. 5a and 5b, the principal optical components of one embodiment of a reflective CTIS include a 2D object scene aperture 231, an unitary primary mirror assembly 248 having a first concave mirror 250 and a second concave mirror 252, a 2D reflective convex diffraction grating 249 having an axis 251, a FPA detector 238 and a pattern 201 for imposing spatial structure. The 2D object scene aperture may include any 2D aperture, including but not limited to squares, rectangles, circles, ellipses, etc., but not including one dimensional apertures such as slits. The plane of the object scene aperture 231 is approximately perpendicular to the grating axis 251. The FPA detector lies in an image focal plane of the object scene aperture 231.

Spatial structure can be imposed in the image in a number of methods. As in the transmissive system, the pattern 201 can be applied directly to the object being imaged, as shown in FIG. 5a, or can be provided at the field stop aperture, as shown in FIG. 5b. In one embodiment, for example, a digital multi-mirror device ("DMM") is inserted at the field stop. Any of the mirrors can be turned on or off to make any desired pattern. In an alternative embodiment, the spatial structure is provided at the field stop aperture in the form of a reflective chrome mask on glass.

In an alternative embodiment, the FPA detector 102 is a color FPA detector. As in the transmissive system, the color FPA detector 238 can take a number of forms and is described in co-pending U.S. patent application titled "COLOR CAMERA COMPUTED TOMOGRAPHY IMAGING SPECTROMETER FOR IMPROVED SPATIAL-SPECTRAL IMAGE ACCURACY," filed Dec. 12, 2006, the entire content of which is incorporated herein by reference. For example, in one embodiment, the color FPA detector 238 may comprise a digital color camera including a digital image sensor, such as a Foveon X3® digital image sensor or a Bayer color filter mosaic. The Foveon X3® digital image sensor includes three layers of pixels (i.e. one red layer, one blue layer and one green layer) on top of each other embedded in a silicon sensor. The Bayer color filter mosaic includes a single layer of a repeating array of red, green and blue filter material deposited on top of each spatial location, and the Bayer color filter mosaic uses twice as many green filters as red or blue filters. In another embodiment, the color FPA detector 238 may include three charge coupled devices ("CCDs"), one for each color: red, green and blue.

In another embodiment, the color FPA detector may comprise any suitable device, such as a monochrome camera or a color camera, over which is positioned a transmission filter that performs a user-defined transmissive function. For example, a color filter adapted to transmit a single color (e.g. red, green or blue) can be positioned over the FPA detector.

The reflective CTIS system can be used in any spectrum. However, as noted above, reflective CTIS systems are particularly useful for operation in the infrared (IR) spectrum. Accordingly, in one embodiment, the color FPA detector comprises a multiple wavelength IR detector.

In one embodiment, the 2D reflective convex diffraction grating 249 comprises a substrate 253 having a convex substrate surface 254 which supports a plurality of grating cells 255 as enlarged and illustrated in FIG. 6. Each grating cell 255 comprises an arrangement of a plurality of pixels 257 as greatly enlarged and illustrated in FIGS. 7a, 7b and 7c. The cells are identical to each other at least in a predetermined zone or area of convex substrate surface 254. In one embodiment, the number of predetermined zones is about four. In another embodiment, the zones are arranged concentrically on the convex substrate surface 254. In FIG. 7a, the reflective surface 259 is on the top of pixels 257, whereas in FIG. 7c, the reflective surface 259 is on the bottom of pixels 257. In all embodiments, however, diffraction occurs as a result of the phase shift due to the varying heights of the pixels 257.

Figure 10A:
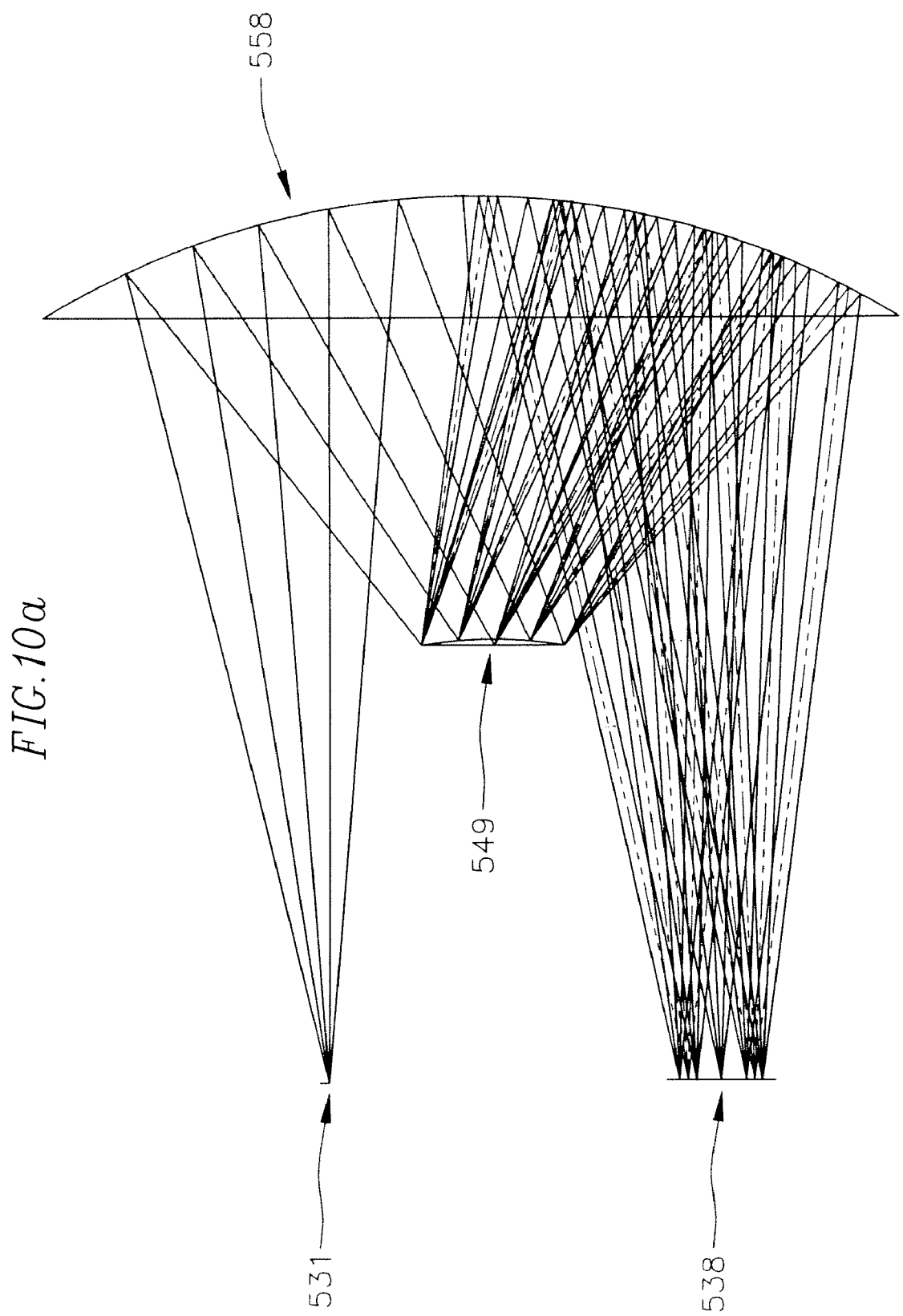
FIG. 10a is a ray-trace plot of a reflective CTIS system, wherein various rays indicate different diffraction orders of the convex grating and not different wavelengths.
Figure 10B:
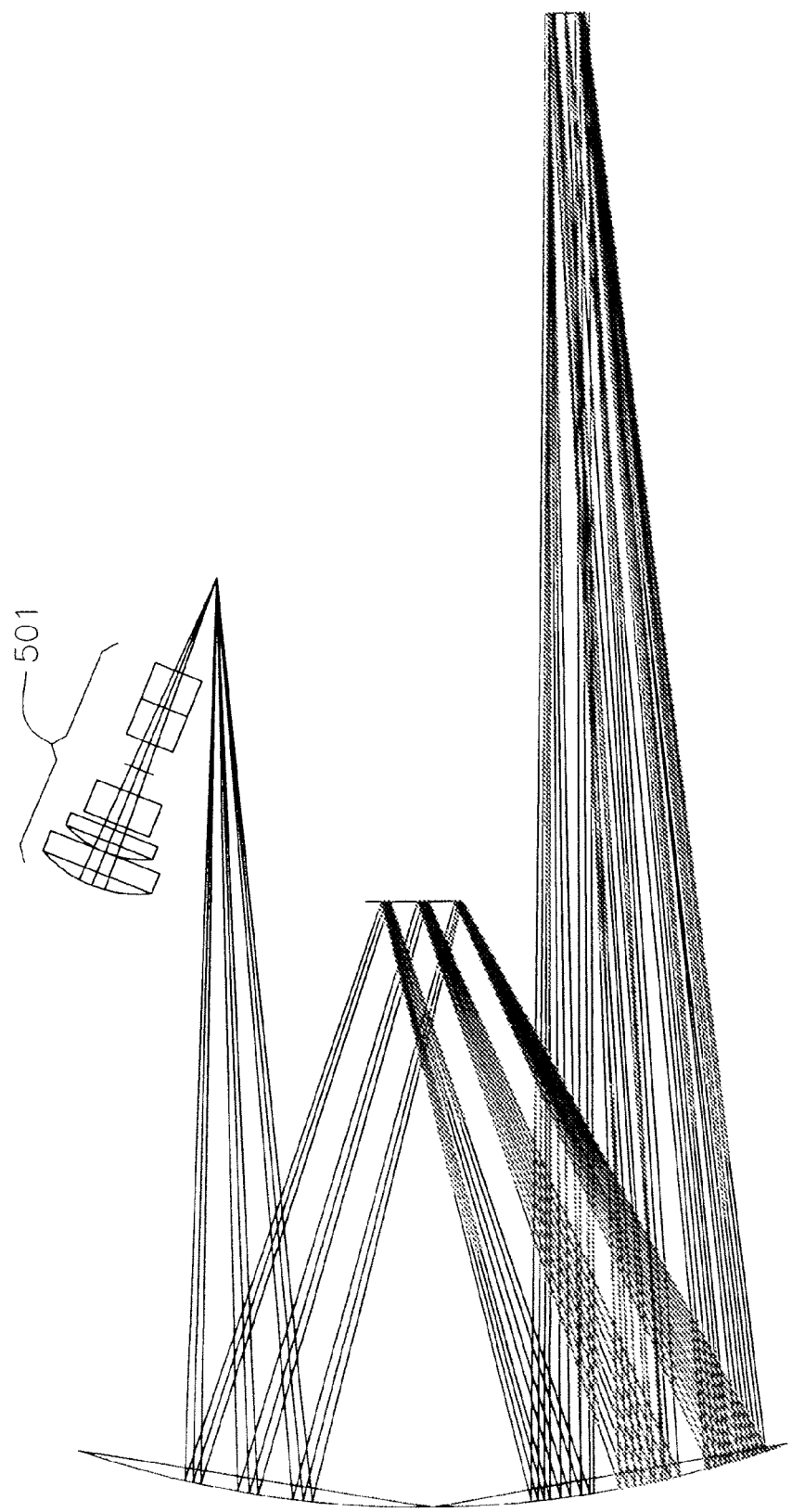
FIG. 10b is a ray-trace plot of a reflective CTIS system utilizing a digital multi mirror device according to one embodiment of the present invention.

In another embodiment of the invention, the 2D reflective diffraction grating 258 is concave, as show in FIG. 7d. The reflective surface can be on the top or bottom of the cells as described with regard to FIGS. 7b and 7c. This particular grating can be used, for example, in a spectrometer not having a primary and tertiary mirror surface, in which the spectra enter aperture 531 and incident directly on the concave reflective grating 558 which diffracts the spectra and focuses the image directly on the FPA detector 538, as shown in FIG. 10.

In one embodiment of the invention, a 2D computer-generated hologram ("CGH") grating is used as the diffraction grating. In one embodiment, the CGH grating is on a convex substrate instead of a one-dimensional blazed grating.

Figure 8:
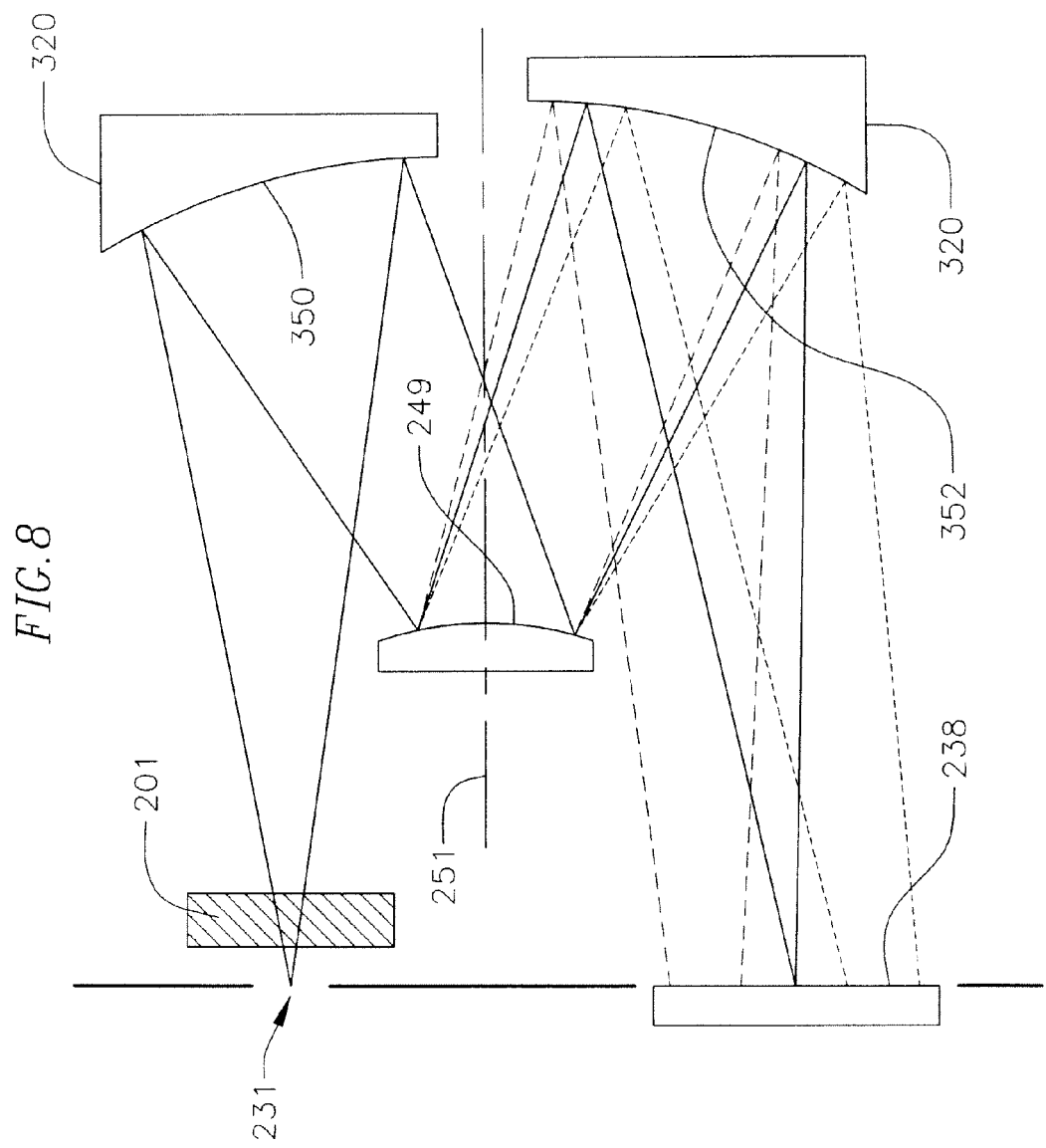
FIG. 8 is a schematic of the principal optical components of a reflective CTIS according to one embodiment of the present invention.

However, for ultraviolet and visible designs, diffraction is not the limiting factor. Imaging aberrations may limit the performance. In one embodiment of the invention for these wavelengths, the large mirror is split into primary and tertiary mirrors that are optimized separately, as shown in FIG. 8. In FIG. 8, the first concave mirror surface 350 of the primary mirror 320 is non-abutting with the second concave mirror surface 352 of the tertiary mirror 321.

Figure 9:
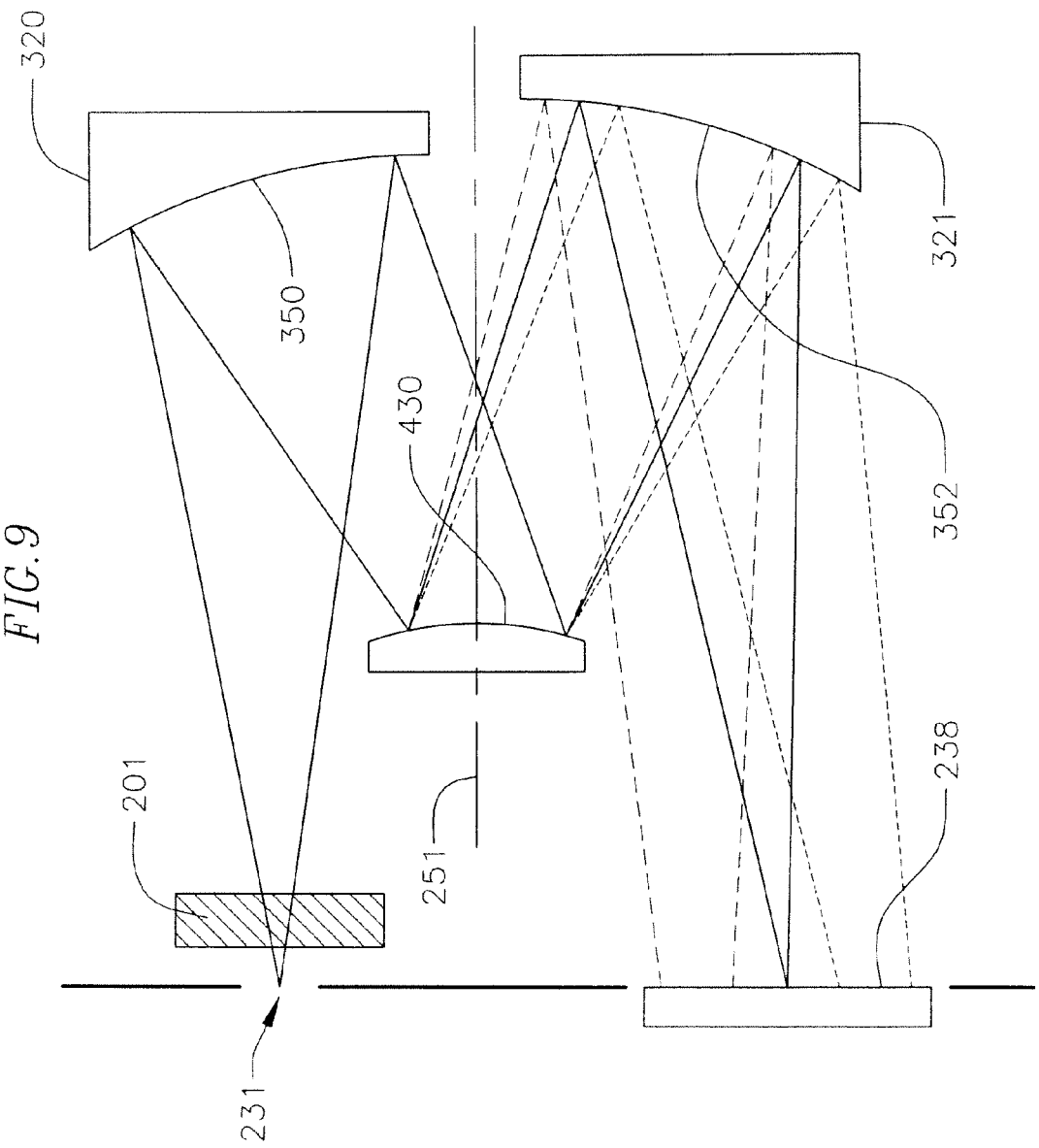
FIG. 9 is a schematic of the principal optical components of a reflective CTIS of the present invention according to yet another embodiment of the present invention including a 2D reflective flat diffraction grating.

Although described principally with respect to an Offner design, the Offner design is not necessary. A traditional three-mirror configuration with a two-dimensional flat reflective diffraction grating 430 can be used for large systems, as shown in FIG. 9.

Figure 11:
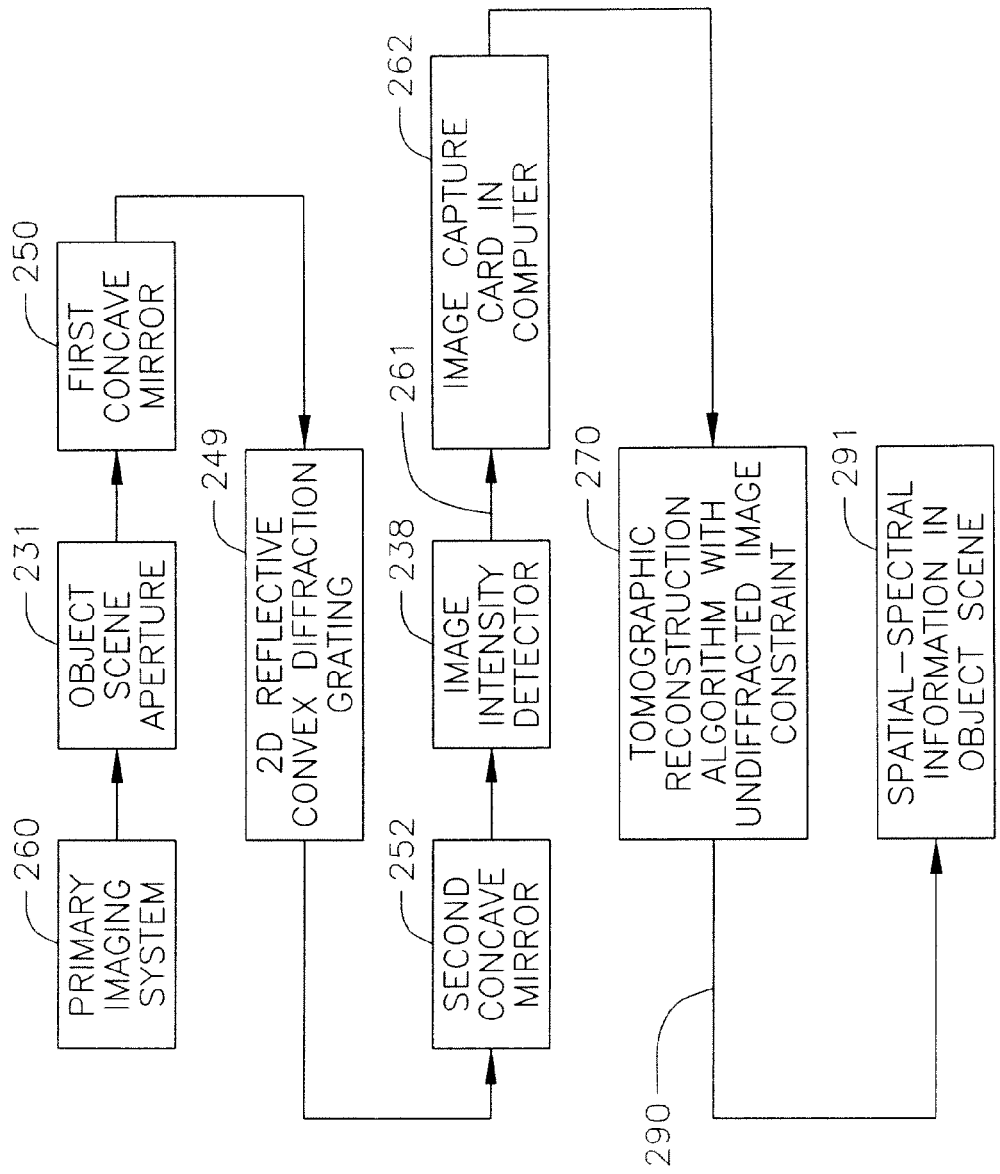
FIG. 11 is an overview of a method according to one embodiment of the invention.

In operation, as shown in FIG. 11, radiation from a primary imaging system 260 is incident upon an object scene aperture 231 and transmitted to the first concave mirror 250. The radiation is reflected from the first concave mirror 250 to the 2D reflective convex diffraction grating 249 where it is further reflected to the second concave mirror 252 which reflects the radiation to the FPA detector 238. A radiation associated signal 261 is then transmitted from the FPA detector 238 to an image capture card 262 in the computer where the signal is processed by a tomographic reconstruction algorithm 270. After a number of iterations, a data stream 290 is produced of spatial-spectral information from the object scene at 291.

Spectra Reconstruction and CTIS Calibration

An algorithm is used to reconstruct the spectra of all the points in the object scene from the captured intensity pattern and knowledge of how points and wavelengths in the field stop map to pixels on the detector. For reflective CTIS systems, spectra reconstruction, in one embodiment, may further include an undiffracted image constraint process. This process includes calculating the predicted undiffracted image based on the current estimate of the scene, then calculating a new set of scaling factors for the scene that force the predicted undiffracted image to equal the measured undiffracted image, and then uniformly scaling the entire scene so that the total number of photons in a predicted detector image remains constant from iteration to iteration.

However, prior to reconstructing the spectra of unknown scenes, the CTIS system must be calibrated. In a conventional monochrome camera system, light entering the field stop is polychromatic, yielding a three-dimensional input to the system, i.e. spatial dimensions x and y, and wavelength dimension $\lambda$. The three dimensional spatial-spectral volume is subdivided into small voxels. Calibration, then, is the determination of which detector pixels are illuminated by a given scene voxel and with what strength (i.e. "scene-voxel to detector-pixel mapping").

This scene-voxel to detector-pixel mapping is represented as a system matrix $H_{sys}$ that has $n_d$ rows and $n_s$ columns, where $n_d$ is the number of detector pixels and $n_s$ is the number of scene voxels. For any given scene $f_{scene}$ composed of voxels $s=1 \ldots n_s$, the detector image $g_{det}$ composed of pixels $d=1 \ldots n_d$ is given by Matrix Equation 1:

$$g_{det} = H_{sys} * f_{scene} \quad (1).$$

In Matrix Equation 1, $f_{scene}$ and $g_{det}$ are arranged as column vectors and all sources of noise have been ignored.

However, in the color camera CTIS according to one embodiment of the present invention, the detector is comprised of three or more color images. Accordingly, the detector image $g_{det}$ is given by Matrix Equation 2:

$$[g_R; g_G; g_B] = [H_R; H_G; H_B] * f_{scene} \quad (2).$$

In Matrix Equation 2, R, G and B indicate the red, green and blue images, respectively. Matrix Equation 2 shows that there are three times the number of equations describing the color camera CTIS as for the monochrome CTIS. This means that the system is more "overdetermined" and better solutions for $f_{scene}$ can result.

To calibrate a conventional monochrome camera system, a combination of measurements with numerical simulations is used. First, the efficiency of the system is measured at all wavelengths, and in all diffraction orders, but at only one spatial location in the field stop. this is done by placing a monochromator-illuminated optical fiber in the center of the field stop, and recording detector images for many wavelengths in the spectral band of interest, e.g. 450-750 nm.

Each of these detector images is then computer analyzed to determine the efficiency, position, and aberrations, if severe, of each diffraction order at the given wavelength. This measurement includes the spectrally dependent transmission of all the optical elements and the responsivity of the color focal plane array detector.

With the system efficiency known, a simulation is used to derive the system transfer matrix H that maps voxels in the field stop to pixels on the detector. This is accomplished by tracing many rays from each voxel through the system, utilizing the measured information and keeping track of the resulting scene-voxel to detector-pixel connection weights. This simulation step can be replaced with actual measurements of scene-voxel to detector-pixel mappings by moving the fiber to each spatial location within the object scene plane. However, this increases the effort significantly and does not allow the voxel sizes (scene resolution) to be adjusted after calibration.

Once the system transfer matrix H is known, unknown scenes can then be imaged and their spectra reconstructed. An iterative expectation-maximization (EM) algorithm can be used, which algorithm was developed for reconstructing positron-emission tomography medical images. However, other known emission tomography algorithms can also be used.

Optical calibration of a color camera CTIS system according to one embodiment of the present invention would proceed in the same manner as the current calibration of monochrome CTIS systems, except that more attention is paid to the specific details of how the color camera FPA is implemented. As noted above, the current monochrome camera technique involves using a monochromator-illuminated fiber to measure the efficiencies, spot centroids, and point-spread functions for all diffraction orders at all wavelengths in the passband of the optical system. This information is then used in a ray-trace simulation to generate the system matrix of scene-voxel to detector-pixel interconnection strengths. The most straightforward color FPA to calibrate would be the Foveon X3® direct image sensor because it uses three layers of pixels on top of one another, each sensitive to a different wavelength region (R, G or B), to measure the color component images. Because there is no spatial dependence of the color detection, no changes to the current calibration scheme would be necessary.

On the other hand, most digital cameras in production today utilize Bayer color filter mosaics to measure the color incident on a 2×2 pixel region, with one red, two green, and one blue filter covering the pixels. Special demosaicing algorithms have been developed to derive the component color images from the filter mosaic images. When calibrating a Bayer FPA, the fiber used to calibrate the system should produce a point-spread function that is at least several 2×2 pixel regions in size to avoid individual filter effects.

The color FPA used for capturing the CTIS dispersed images enables each image pixel to return the fractions of red, green and blue of the incident light. This dramatically benefits the CTIS reconstruction because the component color images exhibit more structure in response to even small changes in spectra compared to the monochrome image which is simply a weighted sum of the color images. This structure presents the reconstruction algorithm with the more difficult task of matching the predicted detector color images (generated by the spatial-spectral image cube) to the measured color detector images. Poor solutions are thus much more effectively rejected and reconstructions having more accurate spectra throughout the scene are obtained. In addition, when using a color FPA detector, using the zero order image as an initial guess gives better and faster results compared to black-and-white monochrome detectors, since the color already contains some spectral data.

Figure 12A:
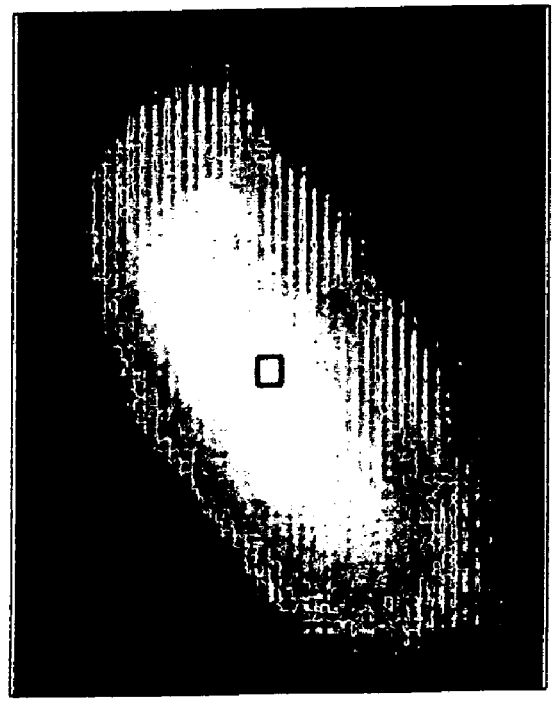
FIG. 12a is a spectrum reconstructed using a prior art CTIS and a HeNe source.
Figure 12A:
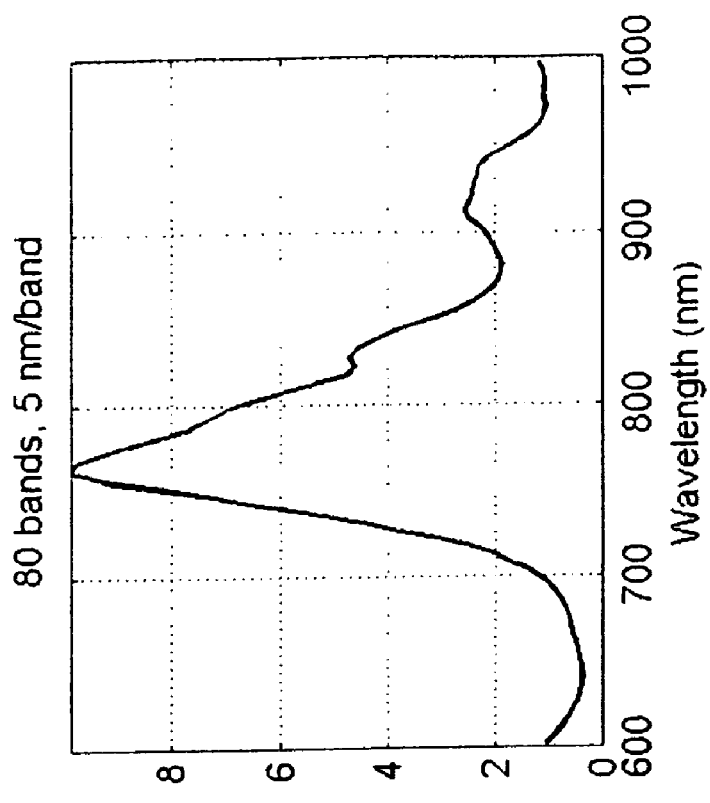
Figure 12B:
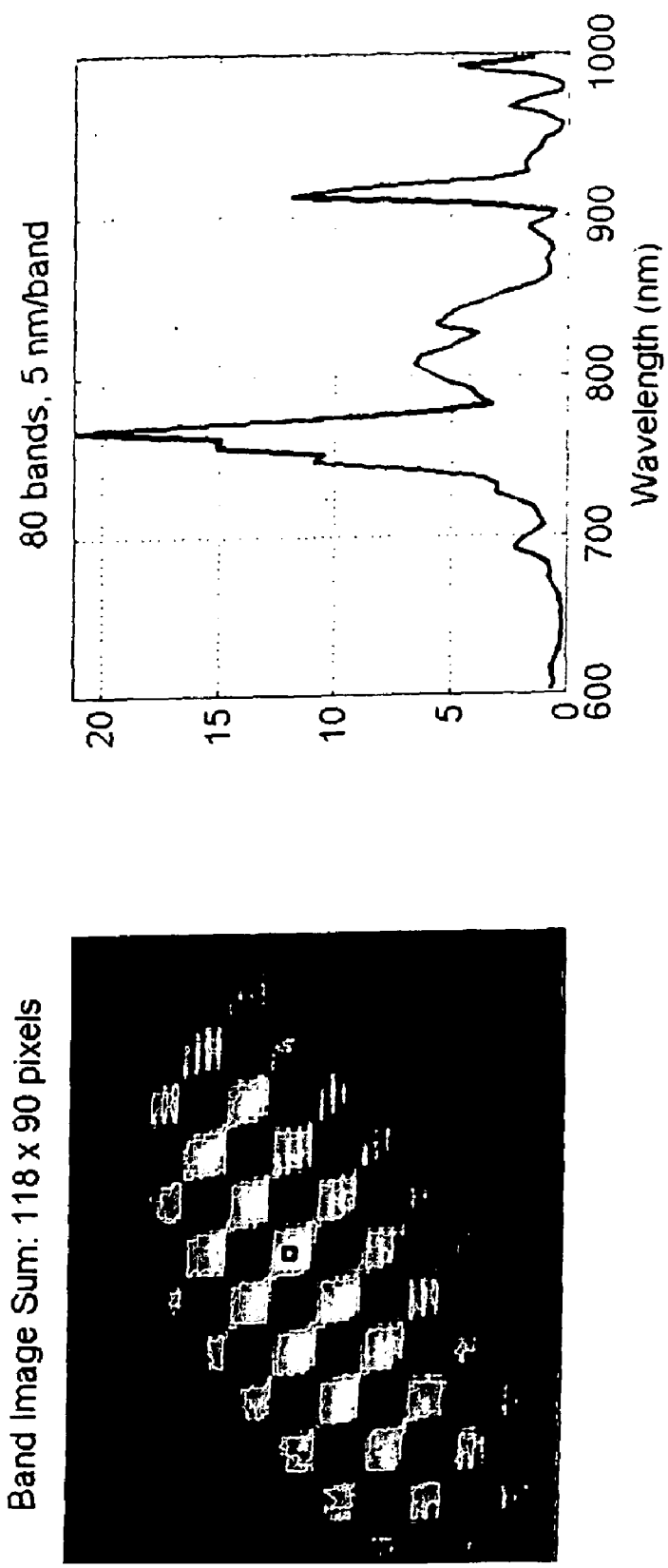
FIG. 12b is a spectrum reconstructed using a CTIS according to one embodiment of the present invention and HeNe source.
Figure 13A:
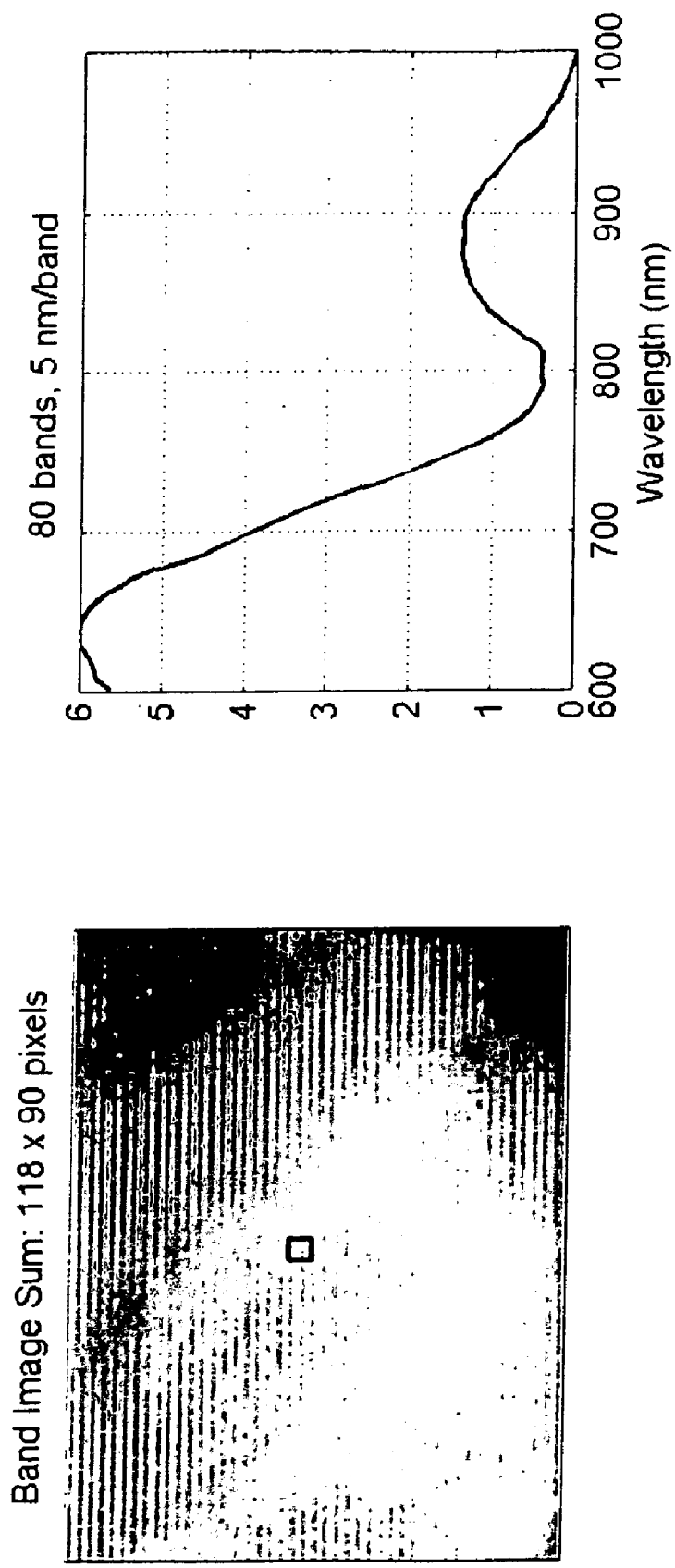
FIG. 13a is a spectrum reconstructed using a prior art CTIS and a LED source.
Figure 13B:
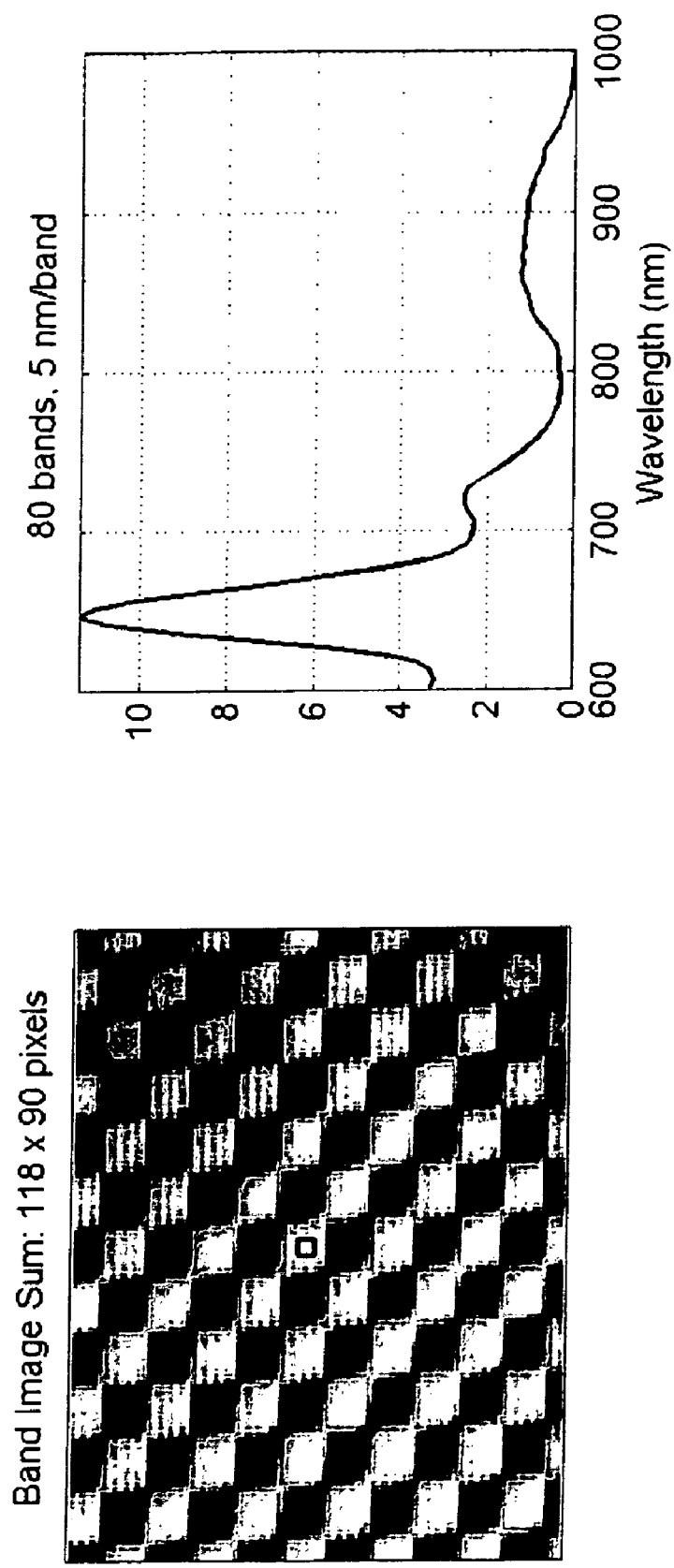
FIG. 13b is a spectrum reconstructed using a CTIS according to one embodiment of the present invention and a LED source.

According to some embodiments of the present invention, the extra structure imparted by the pattern 101 or 201 provides enough data for the algorithm to successfully recover the data. The extra spatial information further improves the spectral reconstruction anywhere in the field. As shown in FIG. 12a, the spectral accuracy of spectra recovered without the use of the pattern according to some embodiments of the present invention are rather poor. In contrast, however, as shown in FIGS. 12b and 13b, the spectral accuracy of spectra recovered using a pattern according to some embodiments of the present invention is much improved, especially at the edges of the field, as shown in FIG. 13b. However, spectral accuracy is also much improved in the center of the field, as shown in FIGS. 12b and 13b.

As noted above, spatial structure can be imposed in the image in a number of methods. For example, a digital multimirror device ("DMM") 501 can be inserted at the field stop in an all-reflective optic version of the CTIS (shown in FIG. 10b). Any of the mirrors can be turned on or off to make any desired pattern. Alternatively, the spatial structure can be a reflective chrome mask on glass, provided at the field stop. In another alternative embodiment, the pattern could be projected onto the imaged object. A full image can be acquired by shifting the pattern with software for the DMM or by moving the mask. Patterns may be used in both the reflective CTIS and the transmissive CTIS.

The preceding description has been presented with reference to certain exemplary embodiments of the present invention. However, workers skilled in the art and technology to which this invention pertains will appreciate that alterations and changes to the described embodiments may be practiced without meaningfully departing from the principal, spirit and scope of this invention. Accordingly, the foregoing description should not be read as pertaining only to the precise embodiments described and illustrated in the accompanying drawings, but rather should be read consistent with and as support for the following claims which are to have their fullest and fairest scope.

What is claimed is:

1. An imaging spectrometer for capturing spatial and spectral information from an object scene comprising:
   a focal plane array detector;
   a primary imaging lens;
   a 2D grating disperser;
   a collimating lens;
   a field stop aperture; and
   a pattern for imposing spatial structure in the object scene,
      wherein light enters the spectrometer through the field stop aperture and passes to the collimating lens, and from the collimating lens to the 2D grating disperser, and through the 2D grating disperser to the primary imaging lens which images the light on the focal plane array detector.

2. The imaging spectrometer according to claim 1, wherein the pattern is positioned on the object scene.

3. The imaging spectrometer according to claim 1, wherein the pattern is positioned at the field stop aperture.

4. The imaging spectrometer according to claim 1, wherein the pattern comprises a checkerboard pattern.

5. The imaging spectrometer according to claim 1, wherein the pattern comprises a grid pattern.

6. The imaging spectrometer according to claim 1, wherein the focal plane array detector comprises a color focal plane array detector.

7. The imaging spectrometer according to claim 6, wherein the color focal plane array detector comprises a transmissive filter adapted to perform a user-identified transmissive function, the transmissive filter positioned over the focal plane array detector.

8. The imaging spectrometer according to claim 6, wherein the color focal plane array detector comprises a digital image sensor comprising three layers of pixels on a detector, the three layers of pixels comprising one layer of red pixels, one layer of blue pixels, and one layer of green pixels.

9. The imaging spectrometer according to claim 6, wherein the color focal plane array detector comprises a color filter mosaic on a detector, the color filter mosaic comprising a single layer of pixels comprising a repeating array of red, green and blue filter materials.

10. The imaging spectrometer according to claim 6, wherein the color focal plane array detector comprises first, second and third charge coupled devices, the first charge coupled device adapted to record red, the second charge coupled device adapted to record blue and the third charge coupled device adapted to record green.

11. An imaging spectrometer for capturing spatial and spectral information from an object scene comprising:
    a focal plane array detector;
    a 2D grating disperser;
    a primary mirror assembly comprising a first concave mirror and second concave mirror;
    a field stop aperture; and
    a pattern for imposing spatial structure in the object scene,
       wherein light enters the spectrometer through the field stop aperture and passes to the first concave mirror of the primary mirror assembly, the light is reflected from the first concave mirror to the 2D grating disperser which reflects the light to the second concave mirror, and wherein the second concave mirror reflects the light to the focal plane array detector.

12. The imaging spectrometer according to claim 11, wherein the pattern is positioned on the object scene.

13. The imaging spectrometer according to claim 11, wherein the pattern is positioned at the field stop aperture.

14. The imaging spectrometer according to claim 11, wherein the pattern comprises a checkerboard pattern.

15. The imaging spectrometer according to claim 11, wherein the pattern comprises a grid pattern.

16. The imaging spectrometer according to claim 11, wherein the focal plane array detector comprises a color focal plane array detector.

17. The imaging spectrometer according to claim 16, wherein the color focal plane array detector comprises a transmissive filter adapted to perform a user-identified transmissive function, the transmissive filter positioned over the focal plane array detector.

18. The imaging spectrometer according to claim 16, wherein the color focal plane array detector comprises a digital image sensor comprising three layers of pixels on a detector, the three layers of pixels comprising one layer of red pixels, one layer of blue pixels, and one layer of green pixels.

19. The imaging spectrometer according to claim 16, wherein the focal plane array detector comprises a color filter mosaic on a detector, the color filter mosaic comprising a single layer of pixels comprising a repeating array of red, green and blue filter materials.

20. The imaging spectrometer according to claim 16, wherein the focal plane array detector comprises first, second and third charge coupled devices, the first charge coupled device adapted to record red, the second charge coupled device adapted to record blue and the third charge coupled device adapted to record green.

21. The imaging spectrometer according to claim 16, wherein the color focal plane array detector comprises a multiple wavelength infrared detector.

* * * * *